United States Patent [19]

Strayer

[11] 4,423,035

[45] Dec. 27, 1983

[54] METHOD FOR PREVENTING INJECTION SITE ABSCESS

[75] Inventor: James G. Strayer, Waterloo, Nebr.

[73] Assignee: Schering Corporation, Kenilworth, N.J.

[21] Appl. No.: 291,157

[22] Filed: Aug. 10, 1981

[51] Int. Cl.³ .............................................. A61K 39/10
[52] U.S. Cl. ......................................... 424/92; 424/88
[58] Field of Search ................ 424/92, 180; 536/17 R

[56] References Cited

U.S. PATENT DOCUMENTS

| | | | |
|---|---|---|---|
| 3,091,572 | 7/1962 | Luedeman et al. | 536/17 |
| 3,419,660 | 12/1968 | Lannon | 424/92 |
| 4,225,583 | 9/1980 | Switzer et al. | 424/92 |
| 4,250,265 | 2/1981 | Carlo et al. | 424/92 |

OTHER PUBLICATIONS

Oden et al., Dev. Biol., 24, 181–187 (1974).
Abstract of the Leptospira bacterin manufactured by Affiliated Labs (Veterinary Pharmaceuticals & Biologicals 76/77).
Abstract of the Pasteurella bacterin manufactured by Affiliated Labs (Veterinary Pharmaceuticals & Biologicals 76/77).
Edison et al., Poultry Science 57, 1519-25 (1978).
Wallack, Nouv. Presse Med. 8, No. 23, 1919–1921 (1979), (with translation).
Koinis et al., Schweiz Rundschau Med. (Praxis) 64, 1176–1179 (1975) (with translation).
Chemical Abstracts, vol. 93, p. 8, Abst. No. 88385h, 1980.

Primary Examiner—Blondel Hazel
Attorney, Agent, or Firm—Bruce M. Eisen; Vincent H. Gifford; Warrick E. Lee, Jr.

[57] ABSTRACT

A method of vaccinating a food producing animal without producing injection site abscess comprising injecting said animal with a vaccine that comprises a bacterin, an effective amount of a compatible adjuvant, an effective amount of a non-antibiotic biocidal compound, and about 30 micrograms per milliliter of gentamicin sulfate.

3 Claims, No Drawings

METHOD FOR PREVENTING INJECTION SITE ABSCESS

The present invention relates to a method for preventing local abscesses that are often a consequence of certain vaccinations. In particular, injection of bacterins, especially those that contain an adjuvant (for example, aluminum hydroxide) dispose the patient to an abscess at the injection site. Corynebacterium pyogenes is generally found to be the infecting organism.

Adjuvants are used in vaccines to slow the diffusion of antigen so that the patient will have time to develop a maximum level of immune response before the entigen is cleared. Examples of typical adjuvants are aluminum hydroxide, aluminum phosphate peanut oil and Freund's complete adjuvant. The preferred amount of adjuvant in each type of vaccine is selected with this goal of maximizing the level of immune response in mind and this amount will be different for each type of vaccine. Of course, an amount of adjuvant that causes less than the maximum response may still be more effective in causing ome improvement in immune response. While an adjuvant may be helpful in maximizing or improving the immune response, it may cause local irritation or tissue damage that will make the injection site more susceptible to development of an abscess. The word "abscess", as used herein, means a septic abscess accompanied by bacterial infection rather than a "sterile" abscess. The latter is a relatively small abscess that is the result of inflammation due to local irritation or tissue damage and is not accompanied by such infection.

The problem of injection site abscess is particularly acute in the large animal field where careful swabbing of the skin before injection and other prophylactic measures are difficult to economically carry out, as even a few remaining microorganisms can cause the problem. Such abscesses are large masses that cause the animal considerable discomfort and may be accompanied by fever if left untreated. The animal's appetite is reduced and weight gain is substantially diminished, resulting in serious economic less to the farmer.

Veterinarians have attempted to prevent abscess formation by adding a therapeutic dose of penicillin or neomycin, e.g. 100 mg or more, to a dose of the bacterin prior to injection. This practice is undesirable for use with food producing animals because of the risk of unacceptable levels of antibiotic residues in the milk or meat. Another approach, used with parenteral Bordetella bronchiseptica bacterins, has been to reduce the concentration of adjuvant in the bacterin. This is undesirable because it may reduce the effectiveness of the bacterin.

I have surprisingly found that adding gentamicin sulfate to a bacterin prior to injection in order to achieve a concentration only of about 30 micrograms per milliliter significantly reduces or eliminates abscess formation at the injection site. This concentration of gentamicin sulfate is quite surprisingly the antiobiotic concentration that is recommended for effectiveness as a preservative.

Although E. Oden et. al., Dev. Biol. 24, 181-187 (1974), have suggested that gentamicin sulfate may be an effective preservative in veterinary biologicals, and although certain bacterins (e.g. Leptospira and Pasteurella bacterins manufactured by Affiliated Laboratories) contain antibiotics such as neomycin as preservatives, there has been no suggestion that adding gentamicin sulfate to a bacterin, at a concentration of about 30 micrograms per mmilliliter, will prevent injection-site abscess.

The present invention thus relates to a method of vaccinating a food producing animal without producing injection site abscess comprising injecting said animal with a vaccine that comprises a bacterin, an effective amount of compatible adjuvant, an effective amount of a non-antibiotic biocidal compound, and about 30 micrograms per milliliter of gentamicin sulfate.

The term "food producing animal" is intended to mean that the milk or meat of the animal (for example, a swine) is generally used for human consumption. The term "non-antibiotic biocidal compound" is intended to mean a chemical compound that is generally used as a preservative in vaccines, but that is not generally referred to by those skilled in the art as an antibiotic. Examples of such compounds are formaldehyde, thimerosol and betapropiolactone.

It will be understood that the purpose "without producing injection site abscess" is not intended to mean that the method of present invention will result in a complete lack of abscess formation in every case. Rather, the method of the present invention will significantly reduce or eliminate such abscess formation. This is true because no method of veterinary treatment can be expected to work one hundred percent of the time. For example, an animal to be vaccinated may be so filthy that there are such substantial numbers of bacteria on its skin that an abscess cannot be totally prevented.

It will be understood that in the context of this invention other antibiotics may be considered as substitutes for gentamicin sulfate if they are found to be equivalent to gentamicin sulfate in their effectiveness against Corynebacterium pyrogenes. Examples of such antibiotics are chloramphemcol, kanamycin, streptomycin, tobramicin, ampicillin, netilmicin, sisomicin, cephalosporins, tetracyclines, and gentamicin as the free base.

It will also be understood that in the context of this invention gentamicin sulfate or its equivalent may also be added to a toxin or antitoxin so that an injection of such toxins or antitoxins will not result in injection site abscess.

EXAMPLE

The following Example illustrates the method of the present invention:

Dissolve 3 milligrams of gentamicin sulfate in one milliliter of distilled water. Add the solution to 100 milliliters of Bordetella bronchiseptica bacterin (manufactured by Burns-Biotec Laboratories, Inc.) before administering the bacterin to swine. The bacterin comprises whole cell cultures of Bordetella bronchiseptica that have been inactivated with a solution of formaldehyde and also contains an aluminum hydroxide adjuvant.

I claim:

1. A method of preventing injection site abscess while vaccinating a food producing animal comprising injecting said animal with a vaccine that comprises inactivated whole cell cultures of Bordetella bronchiseptica, an effective amount of compatible adjuvant, an effective amount of non-antibiotic biocidal compound, and about 30 micrograms per milliliter of gentamicin sulfate.

2. A method according to claim 1, wherein said adjuvant is aluminum hydroxide.

3. A method according to claim 1 or 2 wherein said animal is a swine.

* * * * *